(12) United States Patent
Maier et al.

(10) Patent No.: US 7,582,460 B2
(45) Date of Patent: Sep. 1, 2009

(54) 3-PHOSPHOGLYCERATE DEHYDROGENASE VARIANTS WHOSE INHIBITION BY L-SERINE IS REDUCED, AND GENES ENCODING THEM

(75) Inventors: Thomas Maier, Dachau (DE); Renate Flinspach, Dietramszell (DE)

(73) Assignee: Wacker Chemie AG, München (DE)

( * ) Notice: Subject to any disclaimer, the term of this patent is extended or adjusted under 35 U.S.C. 154(b) by 311 days.

(21) Appl. No.: 10/886,858

(22) Filed: Jul. 8, 2004

(65) Prior Publication Data
US 2005/0009162 A1    Jan. 13, 2005

(30) Foreign Application Priority Data
Jul. 10, 2003   (DE)   ............... 103 31 291

(51) Int. Cl.
 C12N 9/04    (2006.01)
 C12Q 1/00    (2006.01)
 C12Q 1/68    (2006.01)
 C12P 21/04   (2006.01)
 C12N 15/00   (2006.01)
 C12N 1/20    (2006.01)
 C07H 21/04   (2006.01)
 C12Q 1/32    (2006.01)

(52) U.S. Cl. .............. 435/190; 435/4; 435/6; 435/26; 435/69.1; 435/71.1; 435/440; 435/252.3; 435/320.1; 536/23.2

(58) Field of Classification Search .................. None
See application file for complete search history.

(56) References Cited

U.S. PATENT DOCUMENTS 5,618,716 A *  4/1997  Burlingame ............. 435/106
2002/0039767 A1  4/2002  Maier

FOREIGN PATENT DOCUMENTS

| DE | 019949579 | 11/2000 |
|---|---|---|
| DE | 19949579 C1 | 11/2000 |
| DE | 199495194 | 11/2000 |
| DE | 10044 831 | 4/2002 |
| DE | 10044831 A1 | 4/2002 |
| DE | 10232930 | 2/2004 |
| DE | 10232930 A | 2/2004 |
| DE | 10232930 A1 | 2/2004 |
| EP | 0885962 | 12/1998 |
| EP | 0885962 A1 | 12/1998 |
| EP | 0931833 A2 | 7/1999 |
| EP | 0931833 A2 | 7/1999 |
| EP | 0943 687 | 9/1999 |
| EP | 0943687 A2 | 9/1999 |
| WO | 93 12235 | 6/1993 |
| WO | WO93/12235 | 6/1993 |
| WO | WO93/12235 A1 | 6/1993 |
| WO | WO 93/12235 A1 | 6/1993 |
| WO | 9408031 | 4/1994 |
| WO | WO94/08031 | 4/1994 |
| WO | WO 94/08031 | 4/1994 |
| WO | 9715673 | 5/1997 |
| WO | WO 97/15673 | 5/1997 |
| WO | WO97/15673 | 5/1997 |
| WO | 02 061108 | 8/2002 |
| WO | WO02/61108 | 8/2002 |
| WO | WO02/061108 A2 | 8/2002 |

OTHER PUBLICATIONS

Branden et al. introduction to Protein Structure, Garland Publishing Inc., New York, p. 247, 1991.*
Derwent Abstract Corresponding to EP 0 885 962 A1.
Derwent Abstract Corresponding to DE 100 44 831 A1.
Derwent Abstract Corresponding to DE 199 49579 C1.
Derwent Abstract Corresponding to DE 102 32 930A1.
Peters-Wendisch et al., 2002, Appl. Microbiol. Biotechnol. 60: 437-441.
Dubrow & Pizer, 1977, the Journal of Biological Chemistry 252, pp. 1527-1538.
McKitrick and Pizer, 1980, Journal of Bacteriology, Jan. 1980, pp. 235-245.
Grant et al., Journal of Biological Chemistry, vol. 273, No. 35, 28108198, pp. 22389-22394.
Al-Rabiee et al, Journal of Biological Chemistry, vol. 271, No. 22, 1996, pp. 13013-13017.
Grant et al., Journal of Biological Chemistry, vol. 276, No. 2, Jan. 12, 2001, pp. 1078-1083.
Peters-Wendisch et al, 2002, Appl. Microbiol. Biotechnol. 60:437-441.
Dubrow & Pizer, 1977, The Journal of Biological Chemistry 252, pp. 1527-1538.
McKitrick and Pizer, 1980, Journal of Bacteriology, Jan. 1980, pp. 235-245.
Al-Rabiee et al., Journal of Biological Chemistry, vol. 271, No. 22, 1996, pp. 13013-13017, XP 002295412.
Derwent Abstract Corresponding to DE 100 44 831 A1.
Peters•Windisch et al., Appl. Microbiol. Biotechnol. (2002), vol. 60, pp. 437-441.
Dublow & Pizer, The Journal of Biological Chemistry, 1977, vol. 252, No. 5, pp. 1527-1538.
McKitrick & Pizer, Journal of Bacteriology, Jan. 1980, vol. 141, No. 1, pp. 235-245.

(Continued)

Primary Examiner—Yong D Pak
(74) Attorney, Agent, or Firm—Collard & Roe, P.C.

(57) ABSTRACT

A 3-phosphoglycerate dehydrogenase (PGD) which exhibits a susceptibility to inhibition by serine which is reduced a as compared with that of an *Escherichia coli* wild-type PGD and which possesses an amino acid sequence which differs from the amino acid sequence of the *Escherichia coli* wild-type PGD (SEQ ID NO: 2) in that an amino acid apart from glycine is present at position 249 or an amino acid apart from threonine is present at position 372.

2 Claims, No Drawings

OTHER PUBLICATIONS

Grant et al., The Journal of Biological Chemistry, vol. 273, No. 35, Aug. 28, 1998, pp. 22389-22394, XP002295411.
Grant et al., The Journal of Biological Chemistry, vol. 276, No. 2, Jan. 12, 2001, pp. 1078-1083, XP002295413.
Grant et al., Biochemistry 2000, vol. 39, 2000, pp. 7316-7319, XP-002312560.
Schuller et al., Nature Structural Biology, New York, 1995, vol. 2, No. 1, pp. 69-76, XP 009036197.
Al-Rabiee et al., Journal of Biological Chemistry, vol. 271, No. 22, 1996, pp. 13013-13017.
Al-Rabiee et al. "The Mechanism of Velocity Modulated Allosteric Regulation in D-3-Phosphoglycerate Dehydrogenase," The Journal of Biological Chemistry, 1996, vol. 271, No. 38, pp. 23235-23238.
XP002438704 is an extract of the Database UniProt concerning "Predicted dyhydrogenase related to phosphoglycerate dehydrogenase," 2002.
XP002438705 is an extract of the Database UniProt concerning "D-3-phosphoglycerate dehydrogenase" 1998.
XP002438706 is an extract of the Database UniProt concerning "Putative D-3-phosphoglycerate dehydrogenase" 2003.
English Derwent Abstract for DE 100 44 831 A1.
English Derwent Abstract for EP 0 885 962 A1.
English Derwent Abstract for DE 199 49 579 C1.
English Derwent Abstract for DE 102 32 930 A1.
English Derwent Abstract for WO 94/08031.
English Derwent Abstract for WO 97/15673.

* cited by examiner

3-PHOSPHOGLYCERATE DEHYDROGENASE VARIANTS WHOSE INHIBITION BY L-SERINE IS REDUCED, AND GENES ENCODING THEM

CROSS REFERENCE TO RELATED APPLICATIONS

Applicants claim priority under 35 U.S.C. §119 of German Application No. 103 31 291.9 filed Jul. 10, 2003.

BACKGROUND OF THE INVENTION

1. Field of the Invention

The present invention relates to 3-phosphoglycerate dehydrogenase variants whose inhibition by L-serine is reduced, and to genes encoding them.

2. The Prior Art

The twenty natural, protein-forming amino acids are nowadays in the main prepared by fermenting microorganisms. In this connection, use is made of the fact that microorganisms possess appropriate biosynthetic pathways for synthesizing the natural amino acids.

However, in wild-type strains, these biosynthetic pathways are subject to strict control which ensures that the amino acids are only produced to satisfy the endogenous requirement of the cell. An example of an important control mechanism in many biosyntheses is the phenomenon of feedback inhibition (or end product inhibition). In feedback inhibition, it is usually the enzyme in a biosynthetic pathway, which catalyzes the initial enzyme reaction of this biosynthetic pathway, which is inhibited by the end product of the biosynthetic pathway. The inhibition is usually effected by the end product binding allosterically to the enzyme and bringing about a conformational change which converts the enzyme into an inactive state. This thereby ensures that, when the end product accrues in the cell, further synthesis is stopped by the introductory step being inhibited.

It is therefore only possible to produce metabolic products (such as amino acids) efficiently on an industrial scale when the restrictions resulting from the feedback inhibition of a metabolic pathway can be abolished. This will thereby make available microorganisms which, as compared with wild-type organisms, exhibit a drastic increase in their ability to produce the desired metabolic product.

The phosphoglycerate family of amino acids is defined by the fact that these amino acids are derived biosynthetically from 3-phosphoglyceric acid. In this case, the natural path of the metabolism leads initially to L-serine by way of the intermediates 3-phosphohydroxypyruvate and 3-phospho-L-serine. L-serine can be subsequently converted into glycine or else, by way of O-acetylserine, into L-cysteine. L-tryptophan is also to be included in this group since it is likewise derived from the biosynthesis of L-serine. In the same way, unnatural amino acids which are prepared using the method described in US 2002/0039767 A1 are also to be assigned to the phosphoglycerate family.

Compounds which are derived from C1 metabolism are likewise dependent on the biosynthesis of the amino acids of the phosphoglycerate family. This is due to the fact that, when L-serine is converted into glycine, tetrahydrofolate acts as the C1 group acceptor and the loaded tetrahydrofolate is involved, as the central methyl group donor in C1 metabolism, in many biosyntheses (e.g. L-methionine, nucleotides, pantothenic acid, etc.). According to the invention, compounds which are derived from C1 metabolism are consequently preferably compounds whose biosynthesis depends on a C1 group transfer by way of tetrahydrofolic acid.

The initial step in the biosynthesis of amino acids belonging to the phosphoglycerate family is the oxidation of D-3-phosphoglyceric acid to 3-phosphohydroxypyruvate and is catalyzed by the enzyme 3-phosphoglycerate dehydrogenase (PGD) [EC 1.1.1.95]. NAD+, which is converted into NADH/H+, serves as the acceptor for the reducing equivalents which are formed in the reaction.

PGD enzymes are known from a very wide variety of organisms (e.g. *Rattus norvegicus, Arabidopsis thaliana, Escherichia coli, Bacillus subtilis*). The better characterized microbial representatives of these enzymes are subject to feedback inhibition by L-serine.

At the amino acid sequence level, the microbial PGD enzymes are very similar to each other in the N-terminal moiety (amino acids 1-340 in the case of the *E. coli* sequence) whereas the C-terminal moieties only exhibit slight similarities. However, it is precisely in this C-terminal moiety that the regulatory domain which is responsible for the serine inhibition is located (Peters-Wendisch et al., 2002, *Appl. Microbiol. Biotechnol.* 60:437-441).

The PGD which is best characterized is that from *Escherichia coli*. The enzyme has been investigated biochemically in detail (Dubrow & Pizer, 1977, *J. Biol. Chem.* 252, 1527-1538) and is subject to allosteric feedback inhibition by L-serine, with the inhibitor constant Ki being 5 μM.

This feedback inhibition stands in the way of efficiently producing amino acids belonging to the phosphoglycerate family and has therefore already been the target for molecular biological approaches.

Thus, the document EP0620853A described variants of *Escherichia coli* PGD which are less susceptible to inhibition by serine and which exhibit a modification in the C-terminal 25% of the wild-type PGD (i.e. amino acids 307-410), preferably a modification in the region of the last 50 residues (i.e. amino acids 361-410). The mutants which are described were obtained by linker mutagenesis, i.e. by simply making use of restriction cleavage sites which are present in the *E. coli* serA gene and inserting oligonucleotide linkers of 8-14 base pairs in length.

However, such linker mutageneses usually give rise to problems since incorporating, or deleting, several residues very greatly alters the structure of the protein and in this way has a negative influence on the overall activity or stability of the protein. In fact, most of the mutants described in EP0620853A have an activity which is scarcely detectable.

Mutageneses which achieve the goal of decreasing the susceptibility of PGD to inhibition by serine have also been performed on the serA gene in coryneform microorganisms: Peters-Wendisch et al. (2002, Appl. Microbiol. Biotechnol. 60:437-441) describe C-terminal deletions of the *Corynebacterium glutamicum* PGD. In this case, too, the deletions lead to great loss of enzyme activity in some instances.

The application EP0943687A2 describes a replacement of the glutamic acid residue at position 325 in the *Brevibacterium flavum* PGD. In an alignment formed using the GAP algorithm of the GCG (GCG Wisconsin Package, Genetics Computer Group (GCG) Madison, Wis.) program, this residue is already located, with reference to the *Escherichia coli* PGD, in the variable C-terminal moiety of the protein and correlates with the asparagine residue 364 in the *Escherichia coli* protein. Since this modification is located in the variable C-terminal moiety of PGD, it is not possible to draw any conclusions with regard to the *Escherichia coli* protein.

SUMMARY OF THE INVENTION

It is an object of the present invention to make available variants of the *Escherichia coli* PGD which exhibit a susceptibility to inhibition by serine which is reduced as compared with that of the *Escherichia coli* wild-type PGD.

This object is achieved by means of a PGD which has an amino acid sequence which differs from the amino acid sequence of the *Escherichia coli* wild-type PGD (SEQ ID NO: 2), having a methionine as position 1, in that an amino acid apart from glycine is present at position 349 or an amino acid apart from threonine is present at position 372.

A PGD according to the invention can also exhibit mutations at both said positions in SEQ ID NO: 1.

The invention furthermore relates to a DNA sequence which encodes a PGD according to the invention. This serA allele differs from the *Escherichia coli* PGD gene (serA gene, SEQ ID NO: 1) in that codon 349 encodes a natural amino acid apart from glycine or codon 372 encodes a natural amino acid apart from threonine.

A serA allele according to the invention can also possess a mutation at both said codons.

Within the context of the present invention, those genes which, when analyzed using the GAP algorithm (GCG Wisconsin Package, Genetics Computer Group (GCG) Madison, Wis.), exhibit a sequence identity of greater than 30% are also to be regarded as being serA alleles according to the invention, provided they exhibit one of said mutations. Particular preference is given to a sequence identity of greater than 70%.

In the same way, proteins having a sequence identity of greater than 40%, as determined using the GAP algorithm, are to be regarded, within the meaning of the present invention, as being proteins derived from *E. coli* PGD, provided they exhibit PGD activity and one of said amino acid replacements. Particular preference is given to a sequence identity of greater than 70%.

In addition, allele variants of the serA gene which are derived, by the deletion, insertion or replacement of nucleotides, from the sequence depicted in SEQ ID NO: 1, with the enzyme activity of the gene product corresponding to more than 10% of the activity of the wild-type gene product and with a mutation of codon 349, for the amino acid glycine, or of codon 372, for the amino acid threonine, or a combination of the two mutations, being present, are to be understood as being genes according to the invention.

PGD variants which possess an amino acid replacement at position 349 or at position 372, or a combination thereof, can be produced using standard techniques of molecular biology. To do this, mutations are introduced into the PGD-encoding serA gene at the corresponding codons. Appropriate methods for introducing mutations at specific positions within a DNA fragment are known.

The DNA of the *E. coli* serA gene is preferably used as the starting material for the mutagenesis. The serA gene to be mutated can be encoded chromosomally or extrachromosomally. However, preference is given to the serA gene being amplified by the polymerase chain reaction and cloned into a vector. The previously mentioned mutagenesis methods are used to alter one or more nucleotides in the DNA sequence such that the encoded PGD possesses an amino acid replacement at position 349 or 372, with position 1 being the start methionine from SEQ ID NO: 1.

These mutations result in the encoded PGD being less susceptible to inhibition by L-serine (=feedback resistance). In this connection, it is particularly advantageous that the activity of the PGD variants according to the invention in the absence of L-serine is more than 10% of that of the wild-type PGD and is preferably unaltered.

Any method which enables the activity of the enzyme to be determined in the presence of L-serine can be used for determining the extent of the feedback resistance exhibited by a PGD variant according to the invention. For example, the PGD activity can be determined in analogy with the method described by McKitrick and Pizer (1980, *J. Bacteriol.* 141: 235-245). The backward reaction is used to measure the enzyme activity in an assay sample which contains phosphohydroxypyruvate and NADH/H$^+$. The reaction is started by adding enzyme and is monitored in a spectrophotometer by way of the decrease in extinction at 340 nm which is caused by oxidation of the NADH/H$^+$. The inhibition of the activity of the PGD is tested in the presence of various concentrations of L-serine in the reaction mixture. The catalytic activities of the various PGD variants are determined in the presence and absence of L-serine and the inhibitor constants $K_i$ are calculated from these values. The $K_i$ describes the inhibitor concentration at which the activity is only 50% of the activity which was determined in the absence of the inhibitor.

Because of their feedback resistance, PGD enzymes according to the invention can be used to produce amino acids of the phosphoglycerate family or compounds which are derived from the C1 metabolism. For this purpose, the serA alleles according to the invention are expressed in a host strain.

A serA allele according to the invention can be expressed under the control of its own promoter, which is located upstream of the serA gene, or by using other suitable promoter systems which are known to the skilled person. In this connection, the corresponding allele can, for example, be present, under the control of such a promoter, either in one or in several copies on the chromosome of the host organism. The strategies for integrating genes into the chromosome are state of the art. However, preference is given to cloning the serA allele to be expressed into a vector, preferably a plasmid.

The invention therefore also relates to a vector which contains a serA allele according to the invention under the functional control of a promoter.

For the purpose of cloning the serA alleles according to the invention, it is possible to use vectors which already contain genetic elements (e.g. constitutive or regulable promoters and terminators) which make it possible to achieve either continuous expression, or controlled, inducible expression, of the PGD-encoding gene.

In addition, other regulatory elements, such as ribosomal binding sites and termination sequences, and also sequences which encode selective markers and/or reporter genes, are also preferably located on an expression vector. Expression of these selection markers facilitates identification of transformants. Suitable selection markers are genes which encode resistance to, for example, ampicillin, tetracycline, chloramphenicol or kanamycin or other antibiotics. If the serA allele according to the invention is to be replicated extrachromosomally, the plasmid vector should preferably contain an origin of replication. Particular preference is given to plasmid vectors such as the *E. coli* vectors pACYC184, pUC18, pQE-70, pBR322 and pSC101 and their derivatives. Examples of suitable inducible promoters are the lac, tac, trc, lambda PL, ara and tet promoters, or sequences derived therefrom.

In addition, particular preference is given to plasmid vectors which already contain a gene/allele whose use likewise leads to overproduction of amino acids of the phosphoglycerate family or of compounds which are derived from C1 metabolism, such as a gene/allele for producing:

L-serine (e.g. serB gene, serC gene or export carrier gene as described in DE10044831A1)

N-acetylserine, O-acetylserine, cystine, cysteine or cysteine derivatives (e.g. cysE alleles as described in WO97/15673, efflux genes as described in EP0885962A1, cysB gene as described in DE19949579C1 or yfiK gene as described in DE 10232930A)

L-tryptophan (e.g. trpE alleles as described in EP0662143A)

Pantothenic acid (e.g. as described in WO02061108)

These vectors make it possible to directly prepare microorganism strains according to the invention, having high outputs, from any arbitrary microorganism strain, since such a plasmid also neutralizes other restrictions in the metabolic pathway in a microorganism.

A conventional transformation method (e.g. electroporation) is used to introduce the serA allele-containing plasmids according to the invention into microorganisms and, for example, to select, by means of antibiotic resistance, for plasmid-harboring clones.

The invention consequently also relates to a method for producing a microorganism strain according to the invention, which comprises introducing a vector according to the invention into a microorganism strain.

It is also possible to introduce vectors possessing a serA allele according to the invention into microorganisms which, for example, are already expressing, from the chromosome, one or more of the abovementioned genes/alleles and already exhibit overproduction of a metabolic product. In such cases, the introduction of a serA allele according to the invention can increase output still further.

In a general manner, all organisms which possess the pathway for biosynthesizing amino acids of the phosphoglycerate family, which are accessible to recombinant methods and which can be cultured by fermentation are suitable for use as the host organism for vectors according to the invention. These microorganisms can be fungi, yeasts or bacteria. Preference is given to using bacteria of the Eubacteria phylogenetic group. Particular preference is given to microorganisms of the family Enterobacteriaceae and, in particular, of the species *Escherichia coli*.

The invention consequently also relates to a microorganism strain which is suitable for fermentatively producing amino acids of the phosphoglycerate family or their derivatives, or compounds which are derived from C1 metabolism, which strain possesses a PGD according to the invention.

The invention also relates to the production of amino acids of the phosphoglycerate family, or of compounds which are derived from C1 metabolism, by culturing a microorganism strain according to the invention.

For this, the microorganism strain according to the invention is, for example, cultured in a fermenter in a nutrient medium which contains a suitable carbon source and a suitable energy source and also other additives.

The substances which are formed during the fermentation, such as L-phosphoserine, L-serine, O-acetyl-L-serine, L-cysteine, glycine, L-tryptophan, 1,2,4-triazol-2-yl-L-alanine, L-methionine or pantothenic acid, can subsequently be purified.

DETAILED DESCRIPTION OF PREFERRED EMBODIMENTS

The following examples serve to clarify the invention. All of the molecular biological methods employed, such as polymerase chain reaction, the isolation and purification of DNA, the modification of DNA with restriction enzymes, Klenow fragment and ligase, transformation, etc., were carried out in the manner known to the skilled person, in the manner described in the literature or in the manner recommended by the respective manufacturers.

EXAMPLE 1

Cloning the serA Gene

The polymerase chain reaction was used to amplify the serA gene from *Escherichia coli* strain W3110 (American Type Culture Collection, ATCC27325). The oligonucleotides

```
serA-fw: (SEQ ID NO: 3)
5'-gaa ttc cat atg gca aag gta tcg ctg gag-3'
        NdeI
and serA-rev: (SEQ ID NO: 4)
5'-AGA AAG CTT TTA TTA GTA CAG CAG ACG GGC-3'
       HindIII
``` served as specific primers.

The resulting DNA fragment was digested with the restriction enzymes NdeI and HindIII and the 5' overhangs were filled using Klenow enzyme. The DNA fragment was subsequently purified by means of agarose gel electrophoresis and isolated using the GeneClean® method (GeneClean® kit BIO101 P.O. Box 2284 La Jolla, Calif., 92038-2284). The serA fragment which was obtained in this way was cloned into the expression vector pQE-70 (Qiagen, Hilden, Germany). To do this, the vector was first of all cut with SphI and BamHI and the 3' overhang was digested off using Klenow enzyme while the 5' overhang was filled using the Klenow enzyme. The vector fragment was then purified and ligated to the serA fragment. The resulting vector is designated pFL209. After the construct had been verified by sequencing, the *Escherichia coli* strain JM109 (Stratagene, Amsterdam, Netherlands) was transformed and corresponding transformants were selected with ampicillin. The bacterial strain *Escherichia coli* JM109/pFL209 was deposited in the DSMZ (Deutsche Sammlung fur Mikroorganismen und Zellkulturen [German collection of microorganisms and cell cultures] GmbH, D-38142 Braunschweig) under number DSM 15628 in accordance with Budapest Treaty.

EXAMPLE 2

Site-Directed Mutagenesis of the serA Gene

An inverse polymerase chain reaction was used to carry out the site-specific mutagenesis at codons 349 and 372 of the serA gene. The vector pFL209 described in example 1 was used as the template. The primers

```
serA40-mut (SEQ ID NO: 5)
5'-gaa aac cgt ccg nnn gtg cta act gcg-3'
N = G, A, T or C
and serA40-rev (SEQ ID NO: 6)
5'-gtg gat gtg cat cag acg-3'
were used for mutagenizing codon 349.
```

The resulting PCR product was circularized by ligation and transformed into the *E. coli* strain JM109. Finally, sequencing was used to determine the mutation at codon 349 and to check the correctness of the remaining sequence.

In principle, the same procedure was used for mutagenizing codon 372 except that the primers

```
serA20-mut2 (SEQ ID NO: 7)
5'-caa tat ctg caa nnn tcc gcc cag atg gg-3'
N = G, A, T or C
and serA20-rev (SEQ ID NO: 8)
5'-CGC GGC GAT GTT GAC GCC-3'
were used.
```

EXAMPLE 3

Determining PGD Activity and the Inhibitor Constant $K_i$

In order to determine PGD enzyme activities, and the influence of L-serine on the activities, 100 ml volumes of LB medium (10 g of tryptone/l, 5 g of yeast extract/l, 10 g of NaCl/l), which additionally contained 100 mg of ampicillin/l, were in each case inoculated with 2 ml overnight cultures of the strains harboring the plasmid-encoded serA alleles and incubated in a shaker at 30° C. and 150 rpm. At an optical density of 1.0, serA expression was in each case induced by adding 0.4 mM isopropyl-α-thiogalactoside and the culture was incubated for a further 3 hours. The cells were subsequently harvested by centrifugation, washed and resuspended in 2 ml of buffer (100 mM K-phosphate, pH 7.0; 10 mM MgCl2; 1 mM dithiothreitol). The cells were disrupted using a French press (Spectronic Instruments, Inc. Rochester, N.Y., USA) at a pressure of 18 000 psi. The crude extracts were clarified by centrifugation at 30 000 g and PGD activity was determined using the McKitrick and Pizer test (1980, J. Bacteriol. 141:235-245).

The following tables show the PGD activities of different mutants and the corresponding inhibitor constants Ki.

TABLE 1

Mutations at codon 349

| Allele | Mutation | Activity [units/mg] | Ki [mM] |
|---|---|---|---|
| serA | Wild type | 0.05 | <0.1 |
| serA40 | G349 | 0.05 | 25 |
| serA45 | G349I | 0.05 | 5 |
| serA46 | G349M | 0.05 | 1 |
| serA47 | G349E | 0.05 | 20 |
| serA49 | G349P | 0.05 | 6 |
| serA410 | G349S | 0.04 | 2 |
| serA411 | G349T | 0.04 | 3 |
| serA412 | G349V | 0.05 | 5 |
| serA413 | G49L | 0.05 | 5 |
| serA414 | G349A | 0.05 | 1 |
| serA415 | G349K | 0.03 | 15 |
| serA416 | G349R | 0.04 | 15 |
| serA417 | G349W | 0.02 | 8 |
| serA418 | G349Y | 0.05 | 6 |
| serA419 | G349F | 0.05 | 10 |
| serA420 | G349H | 0.05 | 10 |
| serA421 | G349N | 0.05 | 15 |
| serA422 | G349Q | 0.05 | 15 |
| serA445 | G349C | 0.04 | 5 |

TABLE 2

Mutations at codon 372

| Allele | Mutation | Activity [units/mg] | Ki [mM] |
|---|---|---|---|
| serA | Wild type | 0.05 | <0.1 |
| serA20 | T372I | 0.05 | 40 |
| serA21 | T372D | 0.05 | 120 |
| serA11 | T372Y | 0.05 | 35 |
| serA219 | T372G | 0.05 | 8 |
| serA220 | T372S | 0.05 | 1 |
| serA223 | T372E | 0.04 | 150 |
| serA229 | T372R | 0.04 | 120 |
| serA234 | T372K | 0.05 | 110 |
| serA206 | T372P | 0.05 | 120 |
| serA208 | T372H | 0.05 | 80 |
| serA210 | T372W | 0.04 | 60 |
| serA212 | T372F | 0.05 | 60 |
| serA214 | T372A | 0.04 | 10 |
| serA218 | T372N | 0.05 | 100 |
| serA221 | T372Q | 0.05 | 100 |
| serA222 | T372V | 0.05 | 40 |
| serA226 | T372L | 0.04 | 40 |
| serA228 | T372M | 0.03 | 60 |
| serA231 | T372C | 0.02 | 3 |

EXAMPLE 4

Combining the Mutations in Alleles serA20 and serA40

Combining the mutations in condons 349 and 372 should show whether the replacements have a synergistic effect on the feedback resistance. A unique HindIII restriction cleavage site between the two mutation sites was used for this purpose. Thus, HindIII/HindIII restriction of the vector containing the serA20 allele was used to isolate a 183 bp fragment which corresponds to the 3' end of the serA gene and contains the mutation at codon 372. This fragment was cloned into a vector which contained the serA40 allele and which had been digested with HindIII/BamHI, with this thereby resulting in a clone which constituted a double mutant. The following table shows the appurtenant enzyme data.

TABLE 3

Mutations at codons 349 and 372

| Allele | Mutation | Activity [units/mg] | Ki [mM] |
|---|---|---|---|
| serA | Wild type | 0.05 | <0.1 |
| serA2040 | G349D, T372I | 0.05 | 120 |

Accordingly, while a few embodiments of the present invention have been shown and described, it is to be understood that many changes and modifications may be made thereunto without departing from the spirit and scope of the invention as defined in the appended claims.

What is claimed is:

1. An isolated 3-phosphoglycerate dehydrogenase (PGD) which exhibits a susceptibility to inhibition by serine, the inhibition by serine being reduced as compared with that of an *Escherichia coli* wild-type PGD and which possesses an amino acid sequence which differs from the amino acid sequence of the *Escherichia coli* wild-type PGD of SEQ ID NO: 2 solely in that an amino acid selected from the group consisting of I, D, Y, G, S, E, R, K, P, H, W, F, A, N, Q, V, L, M and C is present at position 372 of SEQ ID NO. 2.

2. An isolated 3-phosphoglycerate dehydrogenase which exhibits a susceptibility to inhibition by serine, the inhibition by serine being reduced as compared with that of an *Escherichia coli* wild-type PGD and which possesses an amino acid sequence which differs from the amino acid sequence of the *Escherichia coli* wild-type PGD of SEQ ID NO: 2 solely in that,
    the amino acid D is present at position 349 of SEQ ID NO: 2 and the amino acid I is present at position 372 of SEQ ID NO: 2.

* * * * *

UNITED STATES PATENT AND TRADEMARK OFFICE
CERTIFICATE OF CORRECTION

PATENT NO. : 7,582,460 B2
APPLICATION NO. : 10/886858
DATED : September 1, 2009
INVENTOR(S) : Maier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 451 days.

Signed and Sealed this

Fourteenth Day of September, 2010

David J. Kappos
*Director of the United States Patent and Trademark Office*

SEQUENCE LISTING

<160> NUMBER OF SEQ ID NOS: 8

<210> SEQ ID NO 1
<211> LENGTH: 1233
<212> TYPE: DNA
<213> ORGANISM: Escherichia coli
<220> FEATURE:
<221> NAME/KEY: CDS
<222> LOCATION: (1)..(1230)
<223> OTHER INFORMATION:

<400> SEQUENCE: 1

```
atg gca aag gta tcg ctg gag aaa gac aag att aag ttt ctg ctg gta        48
Met Ala Lys Val Ser Leu Glu Lys Asp Lys Ile Lys Phe Leu Leu Val
1               5                   10                  15 gaa ggc gtg cac caa aag gcg ctg gaa agc ctt cgt gca gct ggt tac        96
Glu Gly Val His Gln Lys Ala Leu Glu Ser Leu Arg Ala Ala Gly Tyr
            20                  25                  30 acc aac atc gaa ttt cac aaa ggc gcg ctg gat gat gaa caa tta aaa       144
Thr Asn Ile Glu Phe His Lys Gly Ala Leu Asp Asp Glu Gln Leu Lys
        35                  40                  45 gaa tcc atc cgc gat gcc cac ttc atc ggc ctg cga tcc cgt acc cat       192
Glu Ser Ile Arg Asp Ala His Phe Ile Gly Leu Arg Ser Arg Thr His
    50                  55                  60 ctg act gaa gac gtg atc aac gcc gca gaa aaa ctg gtc gct att ggc       240
Leu Thr Glu Asp Val Ile Asn Ala Ala Glu Lys Leu Val Ala Ile Gly
65                  70                  75                  80 tgt ttc tgt atc gga aca aac cag gtt gat ctg gat gcg gcg gca aag       288
Cys Phe Cys Ile Gly Thr Asn Gln Val Asp Leu Asp Ala Ala Ala Lys
                85                  90                  95 cgc ggg atc ccg gta ttt aac gca ccg ttc tca aat acg cgc tct gtt       336
Arg Gly Ile Pro Val Phe Asn Ala Pro Phe Ser Asn Thr Arg Ser Val
            100                 105                 110 gcg gag ctg gtg att ggc gaa ctg ctg ctg cta ttg cgc ggc gtg ccg       384
Ala Glu Leu Val Ile Gly Glu Leu Leu Leu Leu Leu Arg Gly Val Pro
        115                 120                 125 gaa gcc aat gct aaa gcg cac cgt ggc gtg tgg aac aaa ctg gcg gcg       432
Glu Ala Asn Ala Lys Ala His Arg Gly Val Trp Asn Lys Leu Ala Ala
    130                 135                 140 ggt tct ttt gaa gcg cgc ggc aaa aag ctg ggc atc atc ggc tac ggt       480
Gly Ser Phe Glu Ala Arg Gly Lys Lys Leu Gly Ile Ile Gly Tyr Gly
145                 150                 155                 160 cat att ggt acg caa ttg ggc att ctg gct gaa tcg ctg gga atg tat       528
His Ile Gly Thr Gln Leu Gly Ile Leu Ala Glu Ser Leu Gly Met Tyr
                165                 170                 175 gtt tac ttt tat gat att gaa aat aaa ctg ccg ctg ggc aac gcc act       576
Val Tyr Phe Tyr Asp Ile Glu Asn Lys Leu Pro Leu Gly Asn Ala Thr
            180                 185                 190 cag gta cag cat ctt tct gac ctg ctg aat atg agc gat gtg gtg agt       624
Gln Val Gln His Leu Ser Asp Leu Leu Asn Met Ser Asp Val Val Ser
        195                 200                 205 ctg cat gta cca gag aat ccg tcc acc aaa aat atg atg ggc gcg aaa       672
Leu His Val Pro Glu Asn Pro Ser Thr Lys Asn Met Met Gly Ala Lys
    210                 215                 220 gaa att tca cta atg aag ccc ggc tcg ctg ctg att aat gct tcg cgc       720
Glu Ile Ser Leu Met Lys Pro Gly Ser Leu Leu Ile Asn Ala Ser Arg
225                 230                 235                 240 ggt act gtg gtg gat att ccg gcg ctg tgt gat gcg ctg gcg agc aaa       768
Gly Thr Val Val Asp Ile Pro Ala Leu Cys Asp Ala Leu Ala Ser Lys
                245                 250                 255
```

```
cat ctg gcg ggg gcg gca atc gac gta ttc ccg acg gaa ccg gcg acc      816
His Leu Ala Gly Ala Ala Ile Asp Val Phe Pro Thr Glu Pro Ala Thr
            260                 265                 270 aat agc gat cca ttt acc tct ccg ctg tgt gaa ttc gac aac gtc ctt      864
Asn Ser Asp Pro Phe Thr Ser Pro Leu Cys Glu Phe Asp Asn Val Leu
            275                 280                 285 ctg acg cca cac att ggc ggt tcg act cag gaa gcg cag gag aat atc      912
Leu Thr Pro His Ile Gly Gly Ser Thr Gln Glu Ala Gln Glu Asn Ile
        290                 295                 300 ggc ctg gaa gtt gcg ggt aaa ttg atc aag tat tct gac aat ggc tca      960
Gly Leu Glu Val Ala Gly Lys Leu Ile Lys Tyr Ser Asp Asn Gly Ser
305                 310                 315                 320 acg ctc tct gcg gtg aac ttc ccg gaa gtc tcg ctg cca ctg cac ggt     1008
Thr Leu Ser Ala Val Asn Phe Pro Glu Val Ser Leu Pro Leu His Gly
                325                 330                 335 ggg cgt cgt ctg atg cac atc cac gaa aac cgt ccg ggc gtg cta act     1056
Gly Arg Arg Leu Met His Ile His Glu Asn Arg Pro Gly Val Leu Thr
            340                 345                 350 gcg ctg aac aaa atc ttc gcc gag cag ggc gtc aac atc gcc gcg caa     1104
Ala Leu Asn Lys Ile Phe Ala Glu Gln Gly Val Asn Ile Ala Ala Gln
        355                 360                 365 tat ctg caa act tcc gcc cag atg ggt tat gtg gtt att gat att gaa     1152
Tyr Leu Gln Thr Ser Ala Gln Met Gly Tyr Val Val Ile Asp Ile Glu
    370                 375                 380 gcc gac gaa gac gtt gcc gaa aaa gcg ctg cag gca atg aaa gct att     1200
Ala Asp Glu Asp Val Ala Glu Lys Ala Leu Gln Ala Met Lys Ala Ile
385                 390                 395                 400 ccg ggt acc att cgc gcc cgt ctg ctg tac taa                          1233
Pro Gly Thr Ile Arg Ala Arg Leu Leu Tyr
                405                 410

<210> SEQ ID NO 2
<211> LENGTH: 410
<212> TYPE: PRT
<213> ORGANISM: Escherichia coli

<400> SEQUENCE: 2

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160
```

-continued

```
His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
                245                 250                 255

His Leu Ala Gly Ala Ala Ile Asp Val Phe Pro Thr Glu Pro Ala Thr
            260                 265                 270

Asn Ser Asp Pro Phe Thr Ser Pro Leu Cys Glu Phe Asp Asn Val Leu
        275                 280                 285

Leu Thr Pro His Ile Gly Gly Ser Thr Gln Glu Ala Gln Glu Asn Ile
290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Val Ile Asp Ile Glu
370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410
```

<210> SEQ ID NO 3
<211> LENGTH: 30
<212> TYPE: DNA
<213> ORGANISM: Artificial Sequence
<220> FEATURE:
<223> OTHER INFORMATION: Primer for PCR

<400> SEQUENCE: 3
gaattccata tggcaaaggt atcgctggag                                30

<210> SEQ ID NO 4
<211> LENGTH: 30
<212> TYPE: DNA
<213> ORGANISM: Artificial Sequence
<220> FEATURE:
<223> OTHER INFORMATION: Primer for PCR

<400> SEQUENCE: 4
agaaagcttt tattagtaca gcagacgggc                                30

<210> SEQ ID NO 5
<211> LENGTH: 27
<212> TYPE: DNA
<213> ORGANISM: Artificial Sequence
<220> FEATURE:
<223> OTHER INFORMATION: Primer for PCR

```
<220> FEATURE:
<221> NAME/KEY: misc_feature
<222> LOCATION: (13)..(15)
<223> OTHER INFORMATION: N = G, A, T or C

<400> SEQUENCE: 5
gaaaaccgtc cgnnngtgct aactgcg                                              27

<210> SEQ ID NO 6
<211> LENGTH: 18
<212> TYPE: DNA
<213> ORGANISM: Artificial Sequence
<220> FEATURE:
<223> OTHER INFORMATION: Primer for PCR

<400> SEQUENCE: 6
gtggatgtgc atcagacg                                                        18

<210> SEQ ID NO 7
<211> LENGTH: 29
<212> TYPE: DNA
<213> ORGANISM: Artificial Sequence
<220> FEATURE:
<223> OTHER INFORMATION: Primer for PCR
<220> FEATURE:
<221> NAME/KEY: misc_feature
<222> LOCATION: (13)..(15)
<223> OTHER INFORMATION: N = G, A, T or C

<400> SEQUENCE: 7
caatatctgc aannntccgc ccagatggg                                            29

<210> SEQ ID NO 8
<211> LENGTH: 18
<212> TYPE: DNA
<213> ORGANISM: Artificial Sequence
<220> FEATURE:
<223> OTHER INFORMATION: Primer for PCR

<400> SEQUENCE: 8
cgcggcgatg ttgacgcc                                                        18
```